United States Patent [19]

Beck et al.

[11] Patent Number: 5,708,180
[45] Date of Patent: Jan. 13, 1998

[54] PROCESS FOR THE PREPARATION OF 2-HALOGENOPYRIDINEALDEHYDES AND NOVEL 2-HALOGENOPYRIDINEALDEHYDES

[75] Inventors: Gunther Beck; Helmut Heitzer, both of Leverkusen, Germany

[73] Assignee: Bayer Aktiengesellschaft, Leverkusen, Germany

[21] Appl. No.: 758,625

[22] Filed: Nov. 27, 1996

Related U.S. Application Data

[63] Continuation of Ser. No. 514,328, Aug. 11, 1995, abandoned.

[30] Foreign Application Priority Data

Aug. 19, 1994 [DE] Germany ............ 44 29 465.4

[51] Int. Cl.⁶ ............ C07D 213/12; C07D 213/48
[52] U.S. Cl. ............ 546/315; 546/250; 546/286; 546/287; 546/314
[58] Field of Search ............ 546/250, 286, 546/287, 314, 315

[56] References Cited

U.S. PATENT DOCUMENTS

| | | | |
|---|---|---|---|
| 4,024,332 | 5/1977 | Fenner et al. | 536/13.8 |
| 4,279,913 | 7/1981 | Baldwin et al. | 514/309 |
| 4,757,073 | 7/1988 | New et al. | 514/252 |
| 4,925,947 | 5/1990 | Cartwright | 546/302 |
| 5,001,138 | 3/1991 | Shiokawa et al. | 514/342 |
| 5,438,033 | 8/1995 | Drumm et al. | 504/130 |

FOREIGN PATENT DOCUMENTS

| | | |
|---|---|---|
| 0001473 | 4/1979 | European Pat. Off. . |
| 0107866 | 5/1984 | European Pat. Off. . |
| 3314196 | 9/1983 | Germany . |
| 9515313 | 6/1995 | WIPO . |

OTHER PUBLICATIONS

Ponticello, G.S., et al, J. Org. Chem. 1979, 44(15), pp. 2702–2704.
J–P. Dulcere, et al., J. Org. Chem., vol. 55, No. 2, pp. 571–575, (1990).
Derwent Abstracts, abstract of JP 04–128,284, (1992).
Derwent Abstracts, abstract of JP 05–017,475, (1993).
M.R.S. Weir, et al., Canadian Journal of Chemistry, vol. 43, pp. 772–782, (1965).
J.J. Krajewski, et al., Canadian Journal of Chemistry, vol. 52, pp. 3626–3630, (1974).
A. Guzman, et al., J. Org. Chem., vol. 55, No. 22, pp. 5793–5797, (1990).
O. Meth–Cohn, et al., J. Chem. Soc. Perkin Trans. I, pp. 1173–1182, (1984).
O. Meth–Cohn, et al., Advances in Heterocyclic Chemistry, vol. 31, pp. 207–236, Academic Press, (1982).
M. Sreenivasulu, et al., Indian Journal of Chemistry, vol. 28B, pp. 584–586, (1989).
M. Aadil, et al., Synthetic Communications, vol. 23, No. 18, pp. 2587–2592, (1993).
M. Mallet, Journal of Organometallic Chemistry, vol. 406, pp. 49–56, (1991).
P–M. Windscheif, et al., Synthesis, pp. 87–92, (1994).
J.S. New, et al., J. Med. Chem., vol. 31, pp. 618–624, (1988).

*Primary Examiner*—Alan L. Rotman
*Assistant Examiner*—Garth M. Dahlen
*Attorney, Agent, or Firm*—Sprung Kramer Schaefer & Briscoe

[57] ABSTRACT

The reaction of cyanoolefins, aminocarbonylolefins or hydroxyiminoolefins with a Vilsmeier reagent leads to 2-halogenopyridines which bear aldehyde groups in the 3 and/or 5 position. These pyridinealdehydes are valuable intermediates for the preparation of pharmaceuticals and crop protection agents.

7 Claims, No Drawings

PROCESS FOR THE PREPARATION OF 2-HALOGENOPYRIDINEALDEHYDES AND NOVEL 2-HALOGENOPYRIDINEALDEHYDES

This application is a continuation of application Ser. No. 08/514,328, filed on Aug. 11, 1995, now abandoned.

The invention relates to a process for the preparation of 2-halogenopyridines bearing aldehyde groups in the 3 and/or 5 position by reacting cyanoolefins, aminocarbonylolefins or hydroxyiminoolefins with a Vilsmeier reagent; the invention further relates to novel 2-halogenopyridinealdehydes.

The few previously known 2-halogenopyridinealdehydes either had to be prepared by multistage syntheses or arose as by-products in only small yields (e.g. U.S. Pat. No. 4,279,913; J. Org. Chem. 55 (1990), 5793; J. Chem. Soc., Perkins Trans. I 1984, 1173). Since they can serve as intermediates for the preparation of pharmaceuticals (U.S. Pat. No. 4,279,913), there was a requirement for an economically expedient preparation process.

It has surprisingly been found that the desired products are accessible via a reaction with a Vilsmeier reagent.

The invention therefore relates to a process for the preparation of compounds of the formula (I)

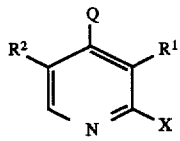

in which

X denotes chlorine or bromine,

Q denotes hydrogen, halogen, $C_1$–$C_8$-alkyl, cyano-$C_1$–$C_8$-alkyl, $C_1$–$C_4$-alkoxy-$C_1$–$C_8$-alkyl, $C_3$–$C_{10}$-cycloalkyl, $C_6$–$C_{12}$-aralkyl, $C_6$–$C_{12}$-aryl, hetaryl having 5 to 7 ring members and 1 to 3 hetero atoms from the group consisting of N, O, S, $R^1$, $R^2$ denote formyl, cyano, hydroxyl, halogen, $C_1$–$C_8$-alkyl, halogeno-$C_1$–$C_8$-alkyl, cyano-$C_1$–$C_8$-alkyl, $C_1$–$C_4$-alkoxy-$C_1$–$C_8$-alkyl, $C_3$–$C_{10}$-cycloalkyl,

$C_6$–$C_{12}$-aralkyl, $C_6$–$C_{12}$-aryl, $C_6$–$C_{12}$-aryloxy, hetaryl having 5 to 7 ring members and 1 to 3 hetero atoms from the group consisting of N, O, S, hetaryloxy having 5 to 7 ring members and 1 to 3 hetero atoms from the group consisting of N, O, S in the hetaryl moiety, with the restriction that at least one of the two substituents $R^1$ and $R^2$ represents formyl, R denotes halogen, $C_1$–$C_4$-alkoxy, phenoxy, —NR'R'' and R', R'' denote, independently of each other, $C_1$–$C_4$-alkyl or both substituents together denote $C_4$–$C_6$-alkylene which can be interrupted by an oxygen atom, characterized in that a compound of the formula (II)

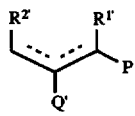

in which the dashed line indicates the two possible position of a C—C bond,

Q' can assume the meanings defined for Q or denotes hydroxyl or $C_1$–$C_4$-alkoxy, P denotes —CN, —CONH$_2$ or —CH=NOH and $R^{1'}$, $R^{2'}$ denote, independently of each other, hydrogen, cyano, halogen, —CONH$_2$, $C_1$–$C_8$-alkyl, halogeno-$C_1$–$C_8$-alkyl, cyano-$C_1$–$C_8$-alkyl, $C_1$–$C_4$-alkoxy-$C_1$–$C_8$-alkyl, hydroxy-$C_1$–$C_8$-alkyl, $C_1$–$C_8$-alkoxy, $C_3$–$C_{10}$-cycloalkyl,

carboxyl, $C_1$–$C_8$-acyloxy, $C_6$–$C_{12}$-aralkyl, $C_6$–$C_{12}$-aryl, $C_6$–$C_{12}$-aryloxy, hetaryl having 5 to 7 ring members and 1 to 3 hetero atoms from the group consisting of N, O, S, hetaryloxy having 5 to 7 ring members and 1 to 3 hetero atoms from the group consisting of N, O, S in the hetaryl moiety with the restriction that at least one of the two substituents $R^{1'}$ and $R^{2'}$ represents hydrogen and R has the meaning specified in formula (I)

is reacted with a Vilsmeier reagent.

In the above definitions

"alkyl" preferably denotes $C_1$–$C_4$-alkyl such as methyl, ethyl,

"halogen" preferably denotes fluorine, chlorine, bromine, in particular chlorine, "halogenoalkyl" preferably denotes halogeno-$C_1$–$C_4$-alkyl such as chloromethyl, 1- and 2-chloroethyl, di- and trifluoromethyl "cyanoalkyl" preferably denotes cyano-$C_1$–$C_4$-alkyl such as cyanomethyl, "alkoxyalkyl" preferably denotes $C_1$–$C_4$-alkoxy-$C_1$–$C_4$-alkyl such as methoxymethyl, "hydroxyalkyl" preferably denotes hydroxy-$C_1$–$C_4$-alkyl such as hydroxymethyl, 1- and 2-hydroxyethyl, "alkoxy" preferably denotes $C_1$–$C_4$-alkoxy such as methoxy, ethoxy, "cycloalkyl" preferably denotes $C_5$–$C_7$-cycloalkyl such as cyclopentyl, cyclohexyl and cycloheptyl, R preferably denotes methoxy, ethoxy and amino groups derived from secondary aliphatic amines such as dimethylamino, diethylamino, pyrrolidino, piperidino, morpholino, hexamethyleneimino, "acyloxy" preferably denotes $C_2$–$C_7$-acyloxy, in particular aliphatic $C_2$–$C_4$-acyloxy, especially acetyl, or benzoyl, "aralkyl" preferably denotes $C_7$–$C_{12}$-aralkyl such as benzyl, 1- and 2-phenethyl, "aryl" preferably denotes $C_6$–$C_{10}$-aryl such as phenyl, naphthyl, "aryloxy" preferably denotes $C_6$–$C_{10}$-aryloxy such as phenoxy, naphthoxy, "hetaryl" preferably denotes 5- and 6-membered ring systems having 1 or 2 hetero atoms from the group consisting of N, O, S, such as 2-, 3- and 4-pyridyl, 2- and 3-thienyl, 2-, 4- and 5-thiazolyl, 2-benzothiazolyl, 2-, 4- and 5-pyrimidyl, where the said rings may be monosubstituted or disubstituted (e.g. by halogen, methyl, methoxy), "hetaryloxy" preferably denotes the radicals analogous to the "hetaryl" radicals.

The starting compounds (II) include, e.g., a) crotononitriles of the formula (IIa)

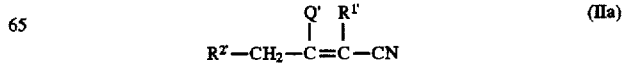

b) allyl cyanides of the formula (IIb)

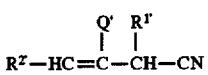 (IIb)

c) crotonamides of the formula (IIc)

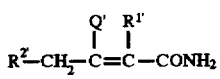 (IIc)

d) but-3-eneamides of the formula

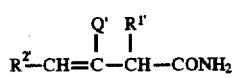 (IId)

d) oximes of crotonaldehydes of the formula

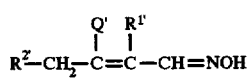 (IIe)

and f) oximes of vinylacetaldehydes of the formula

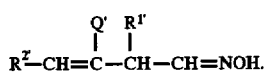 (IIf)

The compounds (II) are known or can be prepared by analogy with known processes.

Preferred starting compounds (IIa) and (IIb) are listed below, by which the analogous compounds (IIc) to (IIf) are also intended to be covered. For better clarity, the starting compounds are subdivided into three groups according to the desired end products.

1. Starting materials for 2-halogeno-3-pyridinecarboxaldehydes:

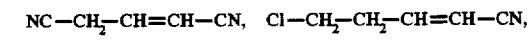
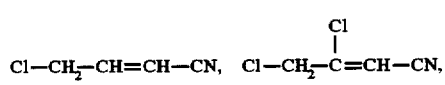
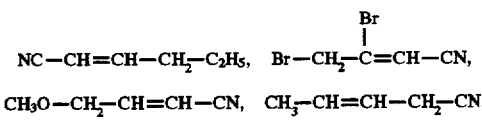
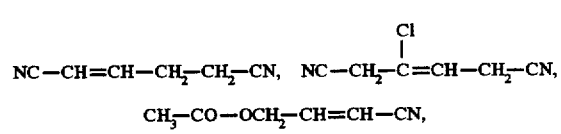

-continued phenyl-CH₂—CH=CH—CH₂—CN,

(R = CH₃, C₂H₅, n-C₃H₇, i-C₃H₇, n-C₄H₉, n-C₆H₁₃,

—CH₂-phenyl, phenyl),

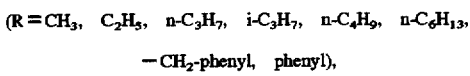

2. Starting materials for 2-halogeno-5-pyridinecarboxaldehydes:

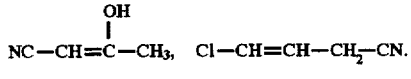

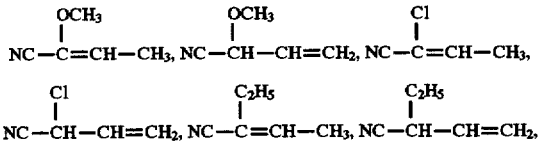

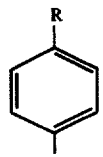
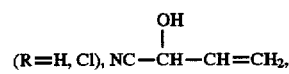

(R=H, Cl), 

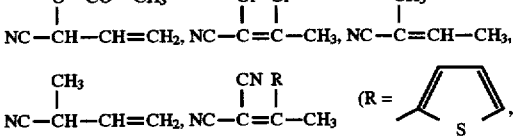

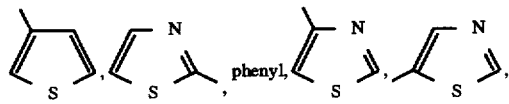 (R = 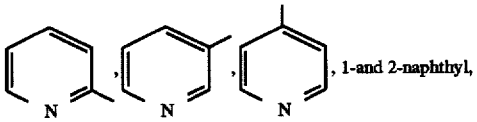

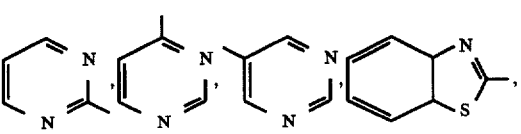, 1-and 2-naphthyl,

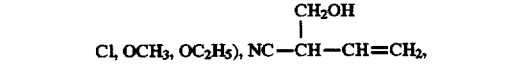

Cl, OCH₃, OC₂H₅), 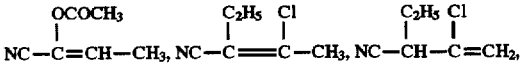

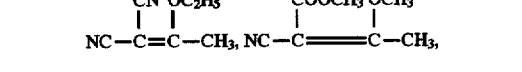

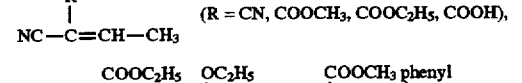

(R = CN, COOCH₃, COOC₂H₅, COOH),

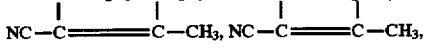

-continued

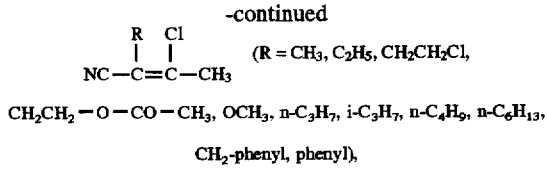

CH₂CH₂—O—CO—CH₃, OCH₃, n-C₃H₇, i-C₃H₇, n-C₄H₉, n-C₆H₁₃,

CH₂-phenyl, phenyl),

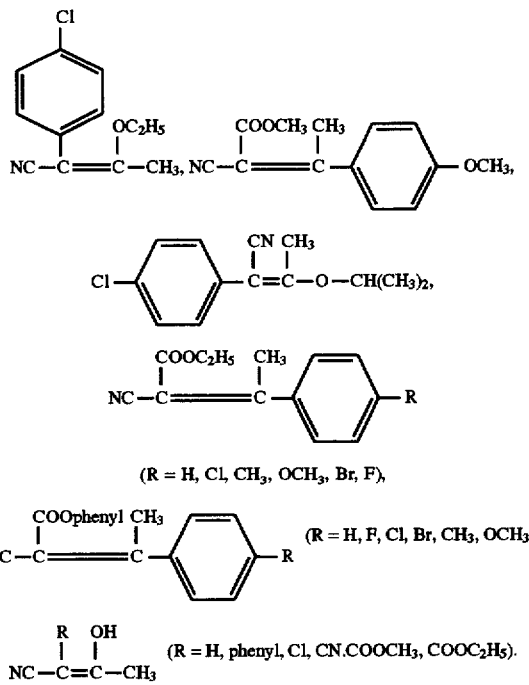

(R = H, Cl, CH₃, OCH₃, Br, F), (R = H, F, Cl, Br, CH₃, OCH₃);

(R = H, phenyl, Cl, CN, COOCH₃, COOC₂H₅).

3. Starting materials for 2-halogeno-3,5-pyridinedicarboxaldehydes:

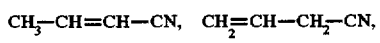

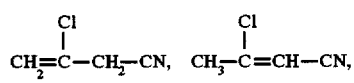

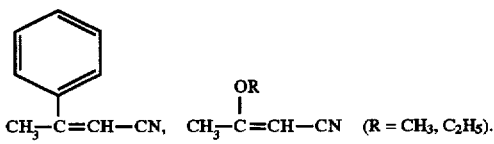 (R = CH₃, C₂H₅).

Particularly preferred starting compounds (II) are those in which Q' denotes hydrogen or chlorine.

Vilsmeier reagents which are useful are the known reaction products of N-formylamides with acid halides. N-formylamides which may be mentioned are for example: dimethylformamide, N-methylformanilide, N-formylpiperidine, N-formylmorpholine. Acid halides which may be mentioned are for example: phosphorus oxychloride, phosphorus oxybromide, phosgene, thionyl chloride, oxalyl chloride. The solvent used can be dimethylformamide, chloroalkanes, chloroalkenes, chlorobenzenes or phosphorus oxychloride or an excess of the Vilsmeier reagent (e.g. produced from phosphorus oxychloride and dimethylformamide) (see in this context: Advances in Heterocyclic Chemistry, vol. 31 (1982), page 207).

The reaction of the compounds (II) with the Vilsmeier reagent can proceed under generally known conditions. Preferably, per mole of the compound (II) at least 2 mol of Vilsmeier reagent are used for the case that $R^{1'}$ or $R^{2'}$=H and P=CN, and at least 3 mol of Vilsmeier reagent for the case that $R^{1'}$ and $R^{2'}$=H and P=CN. However, synthesis of the dialdehyde 2-chloro-3,5-pyridinedicarboxaldehyde shows that even with a deficit of Vilsmeier reagent, e.g. even with 10% of the stoichiometrically required amount, the desired aldehydes I are formed (Example 4).

To achieve the highest possible yield of 2-halogenopyridinealdehydes (I) it can be particularly advantageous to use an excess of Vilsmeier reagent which can be up to 500% of the stoichiometrically required amount. An increase of the reaction time and an increase of the reaction temperature generally effect an increase in yield. Preference is given to reaction temperatures of 0° to 180°, preferably 60° to 160°, in particular 90° to 110° C., and reaction times of about 24 hours, but still longer reaction times up to about 100 hours can be advantageous.

Generally, when the process according to the invention is carded out, N-formylamide, acid halide and starting material (I) are combined at temperatures between about 0° and 5° C., if appropriate further stirred for a period in this temperature range, then gradually (e.g. in the course of one hour) brought to the desired final temperature and further kept at this temperature for the desired reaction time.

However, it is also possible to carry out the process according to the invention at the desired final temperature from the beginning. In this Case, the following method has proved to be particularly simple: the solution of the starting substance in the N-formylamide (preferably dimethylformamide) is added dropwise to the acid halide preheated to the final temperature (e.g. 95° to 100° C.). Ibis process variant is particularly preferred became of its convenient technical manipulation.

During the process according to the invention or the subsequent aqueous work-up of the reaction mixture the substituents which are not inert under these conditions are modified or exchanged, that is to say there is generally formed from —CONH₂: nitrile,
from hydroxyl: halogen (therefore
from hydroxyalkyl: halogenoalkyl),
from acyloxy: hydroxyl and
from carboxyl: COCl.

Alkoxy, in particular methoxy, can be substituted by halogen.

Furthermore, some or all of the COCl groups can be converted into the corresponding carbonamides by the action of the Vilsmeier reagent. Thus, when dimethylformamide is used, from COOH in (II) there can be formed CON(CH₃)₂ in (I).

Some or all activated methylene groups, e.g. NC—CH₂— groups can further react by the action of the Vilsmeier reagent, so that when dimethylformamide is used,

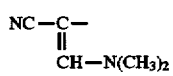

in (I) can be formed from NC—CH₂ in (II).

The process according to the invention is not suggested by the prior art, but is extremely surprising:

In Indian Journal of Chemistry, vol. 28 B, page 584 (1989) it is described that alkylidenemalononitriles can be converted by Vilsmeier reagent into 2-chloro-3-cyanopyridines:

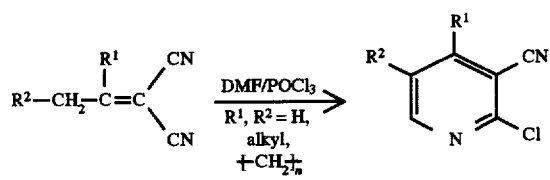

The reaction diagram case where $R^1=R^2=H$, 2-chloro-3-cyanopyridine

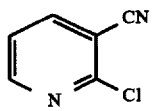

is formed. Instead, according to the invention, 2-chloro-3-cyano-5-pyridinecarboxaldehyde

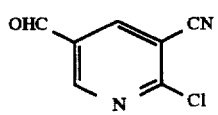

is formed. If one of the two cyano groups in the alkylidenemalononitriles formulated above is replaced by hydrogen, —if there is still a reaction at all owing to the missing second activating nitrile groups—a compound of the formula

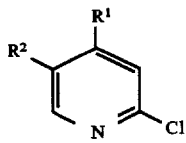

would have been expected. Instead, according to the invention there is formed, for example for the case $R^1=H$, $R^2=CH_3$, 2-chloro-5-methyl-3-carboxaldehyde

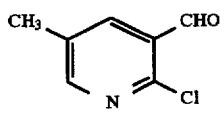

and, for example for the case $R^1=R^2=H$, 2-chloro-3,5-pyridinedicarboxaldehyde

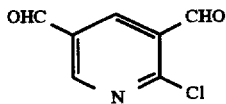

Furthermore, we were able to prove that under the conditions of the process according to the invention no trace of an aldehyde is formed from 2-chloropyridine.

In Synthetic Communications, vol. 23, page 2587 (1993), in analogy with the work cited above, it is described that alkylidenecyanoacetic esters can be converted into 2-chloro-3-pyridinecarboxylic esters by Vilsmeier reagent:

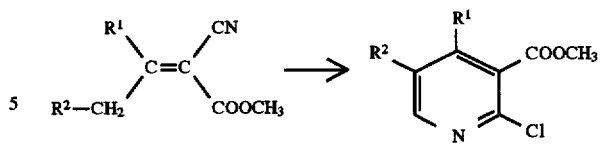

In the work it is asserted that in the case where $R^2=H$, no ring closure takes place.

It could therefore not be predicted that instead according to the invention, for example for the case where $R^1=R^2=H$, the 2-chloro-5-formyl-3-pyridinecarboxylic ester

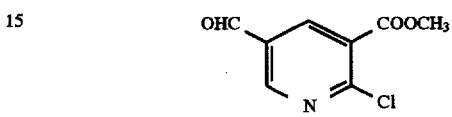

is formed.

Most of the compounds I are novel The invention therefore further relates to compounds of the formula (I) with the exception of 2-chloro-5-methyl-pyridine-3-carboxaldehyde, 2,3-dichloro-pyridine-5-carboxaldehyde and 2-chloro-pyridine-3,5-dicarboxaldehyde.

Preferred compounds I correspond to the formula (III)

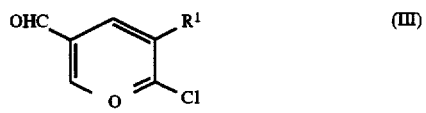

in which $R^1$ represents hydroxy, cyano, methyl, phenyl, chloromethyl, chlorocarbonyl, methoxycarbonyl or ethoxycarbonyl, to the formula

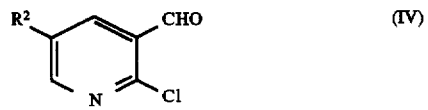

in which $R^2$ represents hydroxy, cyano, chlorine, phenyl, chloromethyl, chlorocarbonyl, methoxycarbonyl or ethoxycarbonyl, to the formula

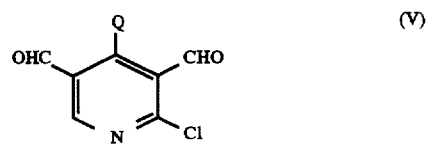

in which

Q represents chlorine or phenyl, or to the formula

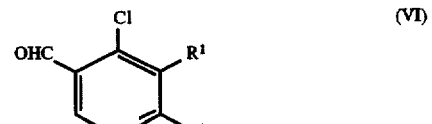

in which $R^1$ represents cyano or phenyl.

The compounds I can be used as intermediates for the preparation of pharmaceuticals and crop protection compounds; see in general K. H. Büchel (editor), Pflanzenschutz und Schädlingsbekämpfung [crop protection and pest control], Georg Thieme Verlag, Stuttgart 1977, substance class "pyridines" (p. 229) and in particular U.S. Pat. No.4, 757,073, German Offenlegungsschrift 24 27 096, 33 14 196, EP-A 1473, 107 866 and 192 060, JP-A05/17475 (26.1.1993) and 04/128 284 (28.4.1992).

The percentages in the following examples are in each case by weight.

EXAMPLES

Example 1

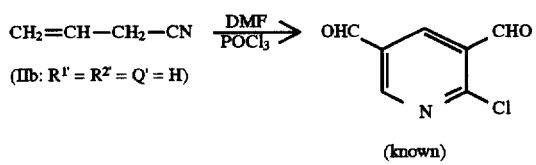

(IIb: $R^{1'} = R^{2'} = Q' = H$)

(known)

A mixture of 26.8 g (0.4 mol) of allyl cyanide and 146 g (2 mol) of dimethylformamide (DMF) is added dropwise to 307 g (2 mol) of phosphorus oxychloride with stirring and the exclusion of moisture at 95° to 100° C. in the come of one hour. The mixture is stirred for a further 24 hours at 95° to 100° C. After cooling to about 20° C. the mixture is first stirred with 500 ml of dichloromethane and then 500 ml of water is added under cooling in such a way that the internal temperature does not exceed 25° C. The organic phase is separated off and the aqueous phase is further extracted three times each time with 250 ml of dichloromethane. The combined dichloromethane phases are washed twice each time with 500 ml of water, dried over sodium sulphate and concentrated in a rotary evaporator. 34.2 g (50.4% of theory) of 2-chloro-3,5-pyridinedicarboxaldehyde remain having a GC purity of 98%. After recrystallization from cyclohexane, long thin needles of melting point 77° to 78° C. In J. Org. Chem. 55 (1990), 5793, a melting point of 70° to 71° C. is quoted: the IR and $^1$H-NMR data cited there agree with those found here.

Example 2

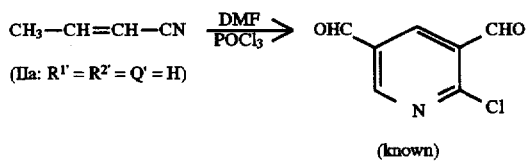

(IIa: $R^{1'} = R^{2'} = Q' = H$)

(known)

The procedure is carded out by analogy with Example 1 with the difference that instead of 26.8 (0.4 mol) of allyl cyanide, 26.8 g (0.4 mol) of crotononitrile are used. 2-Chloro-3,5-pyridinedicarboxaldehyde is obtained in virtually identical yield and purity.

Example 3

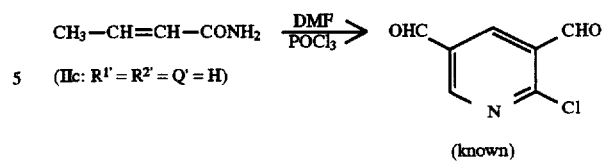

(IIc: $R^{1'} = R^{2'} = Q' = H$)

(known)

The procedure is carded out by analogy with Example 1 with the difference that instead of 26.8 g (0.4 mol) of allyl cyanide, 34 g (0.4 mol) of crotonamide are used. 2-Chloro-3,5-pyridinedicarboxaldehyde is obtained in virtually identical yield and purity.

Example 4

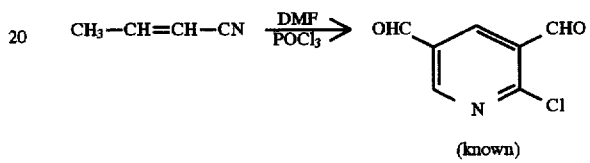

(known)

This Example demonstrates that the dialdehyde is formed even with a deficit of Vilsmeier reagent:

The procedure is followed by analogy with Example 1 with the difference that instead of 26.8 g (0.4 mol) of allyl cyanide, 26.8 g (0.4 mol) of crotononitrile are used and instead of 146 g (2 mol) of DMF, only 40.9 g (0.56 mol equivalent to about 47% of the stoichiometrically required amount) of DMF are used. After further stirring for three hours at about 100° C., the mixture is cooled to 25° C. and the excess phosphorus oxychloride is taken off in vacuo at a bath temperature of 25° C. Further work-up is performed in a similar manner to Example 1. 12.8 g of a mixture are obtained which according to GC/MS analysis comprises about 35% starting product, about 14% of 3-chlorobutyronitrile (HCl-addition product on crotononitrile) and 45% of 2-chloro-3,5-pyridinedicarboxaldehyde. The two monoaldehydes 2-chloro-3-pyridinecarboxaldehyde and 2-chloro-5-pyridinecarboxaldehyde were detected at 1.3% and 0.5%. 2-Chloropyridine was not found.

Example 5

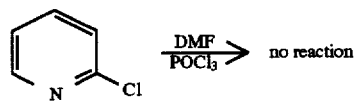

This Example demonstrates that the synthesis of 2-chloro-3,5-pyridinedicarboxaldehyde from allyl cyanide or from crotononitrile does not proceed via the intermediate 2-chloropyridine:

A procedure is followed by analogy with Example 1 with the difference that instead of 26.8 g (0.4, mol) of allyl cyanide, 45.4 g (0.4 mol) of 2-chloropyridine are used. The crude product obtained, according to GC/MS analysis, does not contain any trace of a 2-chloropyridinemonoaldehyde or 2-chloropyridinedialdehyde.

Example 6

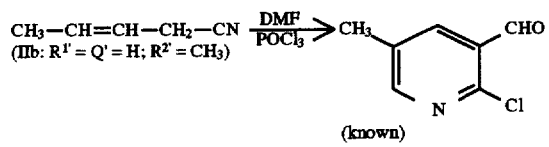

A procedure is followed by analogy with Example 1 with the difference that, instead of 26.8 g (0.4 mol) of allyl cyanide, 72.9 g (0.9 mol) of trans-pent-3-enenitrile are used. 65.6 g of a crude product are obtained which, according to GC-MS analysis, comprises 72.5% (equivalent to 34% of theory) of 2-chloro-5-methyl-3-pyridinecarboxaldehyde. After recrystallization from cyclohexane, needles of melting point 114° to 114.5° C. In J. Chem. Soc., Perkin Trans. I 1984, 1173, a melting point of 114° to 115° C. is given; the IR and $^1$H-NMR data cited there agree with those found here.

Example 7

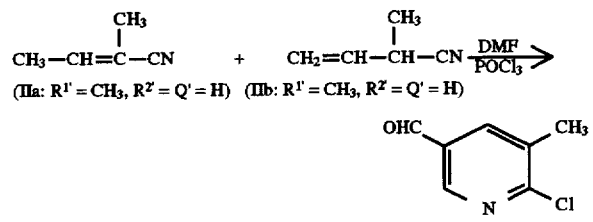

The procedure is followed by analog with Example 1 with the difference that, instead of 26.8 g (0.4 mol) of allyl cyanide, 72.9 g (approximately 0.84 mol) of a mixture are used which, according to $^1$H-NMR analysis, comprises 54.3 mol per cent of 2-methyl-but-2-enenitrile, 38.7 mol per cent of 2-methyl-but-3-enenitrile and 7.0 mol per cent of cyclohexane (Fluka). The dichloromethane phase is concentrated in vacuo on a rotary evaporator at a final bath temperature of 60° C.; 44.1 g of an oil remain which solidifies on cooling and, according to GC/MS analysis, comprises 61.2% (equivalent to 20.7% of theory) of 2-chloro-3-methyl-5-pyridinecarboxaldehyde and about 24% of readily volatile components, including the starting materials whose formulae are given above. The latter are taken off at approximately 0.1 mbar and a bath temperature of 60° to 70° C., and the cooled residue is recrystallized from petroleum ether. Melting point 54° C.

| $^1$H—NMR (CDCl$_3$) | |
|---|---|
| H | δ (ppm) |
| H at C-4 | 8.05(d) - J4.6 ≈ 2 Hz |
| H at C-6 | 8.72(d) - J4.6 ≈ 2 Hz |
| CHO | 10.10(s) |
| CH$_3$ | 2.50(s) |

Example 8

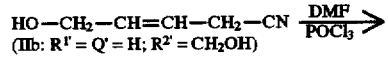

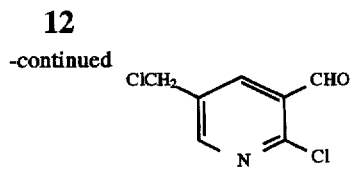

A mixture of 19.4 g (0.2 mol) of 5-hydroxy-trans-pent-3-enenitrile and 32.1 g (0.44 mol) of DMF are added dropwise to 307 g (2 mol) of phosphorus oxychloride with stirring and in the absence of moisture with ice-bath cooling at 0° to 5° C. in the course of about 30 minutes. The mixture is then heated to 100° C. in the course of one hour and kept at this temperature for a further 3 hours. The mixture is then cooled and the excess POCl$_3$ is taken off in vacuo at a bath temperature of 25° C. Further work-up is performed by analogy with Example 1. 19.8 g of an oil are obtained which, according to GC/MS analysis, comprises 17.7% of 5-chloro-3-pentenenitrile and 74.4% of 2-chloro-5-chloromethyl-3-pyridinecarboxaldehyde (equivalent to 45.6% of theory, based on unreacted starting product). Fractional distillation at 101° C./0.15 mbar gives a 97.8% pure, according to GC, 2-chloro-5-chloromethyl-3-pyridinecarboxaldehyde which solidifies on cooling. Melting point 45.5° to 46° C. after recrystallization from petroleum ether (b.p. 30°–50° C.).

| $^1$H—NMR (CDCl$_3$) | |
|---|---|
| H | δ (ppm) |
| H at C-4 | 8.27(d) |
| H at C-6 | 8.65(d) |
| CHO | 10.45(s) |
| CH$_2$Cl | 4.66(s) |

Example 9

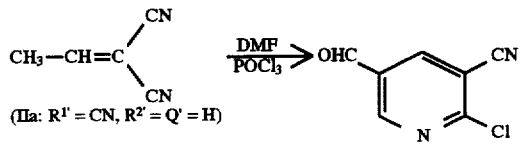

A mixture of 292 g (4 mol) of DMF and 102 g (0.887 mol) of crude, 80% pure, according to GC analysis, (remainder benzene) 2-cyano-but-2-enenitrile is added dropwise with stirring to 614 g (4 mol) of phosphorus oxychloride in the absence of moisture with ice-bath cooling at 20° to 25° C. in the course of 40 minutes. The mixture is then heated in the course of one hour to 95° to 100° C. and kept at this temperature for a further 24 hours. After cooling, the mixture is worked up in accordance with Example 1 (with respective doubling of the amounts of dichloromethane and water specified there). 24.2g (16.4% of theory) of 2-chloro-3-cyano-5-pyridinecarboxaldehyde are obtained as a crystalline product at a GC purity of 95.2%. Melting point 96° C. after recrystallization from cyclohexane.

The 2-cyano-but-2-enenitrile was prepared starting from 1 mol of malodinitrile and 1.4 mol of acetaldehyde in 1000 ml of benzene with the addition of 0.1 ml of diethylamine in accordance with the details in Can. J. Chem. 43, 773 (1965), but, became of its known high tendency to trimerization [compare Can. J. Chem. 52, 3626 (1974)], not distilled but used as crude product. Yield of 2-chloro-3-cyano-5-pyridinecarboxaldehyde over both stages, based on 1 mol of malodinitrile: 14.5% of theory.

| ¹H—NMR (CDCl₃) | |
| --- | --- |
| H | δ (ppm) |
| H at C-4 | 8.48(d) |
| H at C-6 | 9.05(d) |
| CHO | 10.15(s) |

| ¹H—NMR (CDCl₃) | |
| --- | --- |
| H | δ (ppm) |
| H at C-4 | 8.47(d) |
| H at C-6 | 8.85(d) |
| CHO | 10.05(s) |
| COO$\underline{CH_2}$CH₃ | 4.33(q) |
| COOCH₂$\underline{CH_3}$ | 1.32(t) |

Example 10

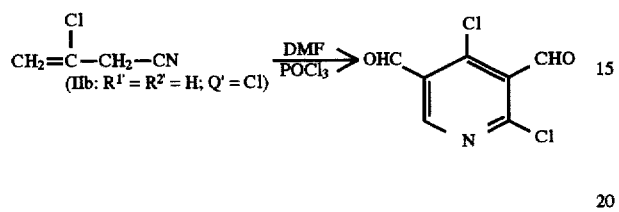

The procedure is followed by analogy with Example 1 with the difference that, instead of 26.8 g (0.4 mol) of allyl cyanide, 30.45 g (0.3 mol) of 3-chloro-but-3-enenitrile are used. 36.1 g of a crude product are obtained which, according to GC/MS analysis, comprises 75.6% (equivalent to 44.6% of theory) of 2,4-dichloro-3,5-pyridinedicarboxaldehyde. After recrystallization from cyclohexane, a pure product of melting point 89° to 90° C. is obtained.

In the crude product, 2.9% of 2,4-dichloro-5-pyridinecarboxaldehyde and 7.8% of 2,4-dichloro-3-pyridinecarboxaldehyde could be detected by GC/MS analysis. A slight excess of Vilsmeier reagent increases the relative proportion of these two monoaldehydes. 2,4-Dichloropyridine is not detected in any case.

| ¹H—NMR (CD₃—CN) | |
| --- | --- |
| H | δ (ppm) |
| H at C-6 | 8.87(s) |
| CHO at C-3 | 10.45(s) |
| CHO at C-5 | 10.40(s) |

Example 11

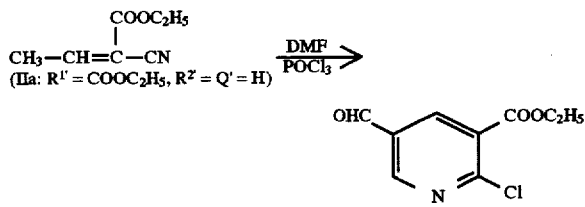

A procedure is followed by analogy with Example 1 with the difference that, instead of 26.8 g (0.4 mol) of allyl cyanide, 75.2 g (0.6 mol) of 92.6% pure, distilled ethyl ethylidenecyanoacetate are used. 60.0 g of a crude product are obtained which is pitied by fractional vacuum distillation. The main fraction boils at 122° C./0.07 mbar. GC purity 93%, yield 32.7 g (equivalent to 28.5% of theory, based on 100% purity).

Example 12

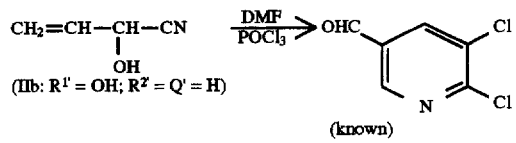

(known)

A procedure is followed by analogy with Example 1 with the difference that, instead of 26.8 g (0.4 mol) of allyl cyanide, 41.5 g (0.5 mol) of 2-hydroxy-but-3-enenitrile are used. 46.6 g of a crude product are obtained which, according to GC/MS analysis, comprises 75.7% (equivalent to 40.1% of theory) of 2,3-dichloro-5-pyridinecarboxaldehyde. After recrystallization from cyclohexane, colourless needles of melting point 68° C.

| ¹H—NMR (CDCl₃) | |
| --- | --- |
| H | δ (ppm) |
| H at C-4 | 8.26(d) |
| H at C-6 | 8.78(d) |
| CHO | 10.10(s) |

In the crude product, 15.3% of 2,5-dichloro-3-pyridinecarboxaldehyde are detected by GC/MS analysis. This compound, according to the diagram

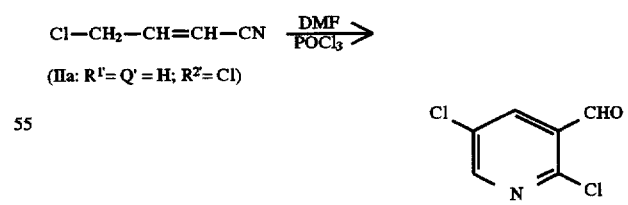

is formed from 4-chloro-but-2-enenitrile which, in addition to 2-chloro-but-3-enenitrile, is known to be formed from 2-hydroxy-but-3-enenitrile (=cyanohydrin of acrolein) by the action of Vilsmeier reagent (compare J. Org. Chem. 55, (1990), 571).

Example 13

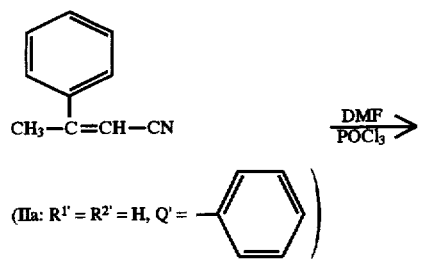

(IIa: R¹' = R²' = H, Q' = —⌬)

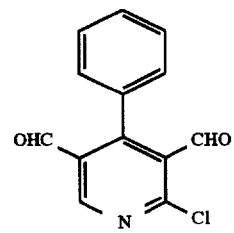

Firstly, a procedure is followed by analogy with Example 1 with the difference that, instead of 26.8 g (0.4 mol) of allyl cyanide, 28.6 g (0.2 mol) of 3-phenyl-but-2-enenitrile are used. After the addition of the DMF/nitrile mixture, the mixture is heated up to a final temperature of about 160° C. in the course of 3 hours, then cooled to room temperature and worked up by analogy with Example 1. 33.2 g of a reaction mixture are obtained in which, apart from the starting product, inter alia the following compounds were detected:

2-chloro-4-phenyl-3-pyridinecarboxaldehyde,
2-chloro-4-phenyl-5-pyridinecarboxaldehyde and
2-chloro-4-phenyl-3,5-pyridinedicarboxaldehyde.

Example 14

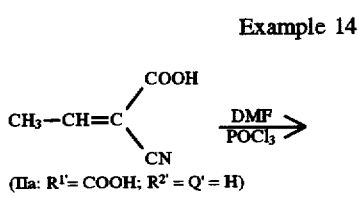

(IIa: R¹' = COOH; R²' = Q' = H)

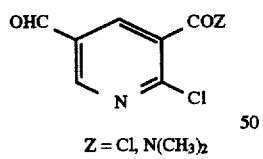

Z = Cl, N(CH₃)₂

A solution of 22.2 g (0.2 mol) of ethylidenecyanoacetic acid in 29.2 g (0.4 mol) of DMF is added dropwise with stirring to 307 g (2 mol) of phosphorus oxychloride in the absence of moisture with ice cooling at 0° to 5° C. in the come of about 30 minutes. The mixture is then heated to 100° C. in the course of one hour and kept at this temperature for a further 3 hours. The mixture is then cooled and the excess POCl₃ is taken off in vacuo at a bath temperature of 25° C. Further work-up is performed by analogy with Example 1. 21.6 g of an oil are obtained whose two main components, according to GC/MS analysis, comprise 25.7% of 2-chloro-3-chlorocarbonyl-5-pyridinecarboxaldehyde and 57.1% of 2-chloro-3-N,N-dimethylaminocarbonyl-5-pyridinecarboxaldehyde.

Example 15

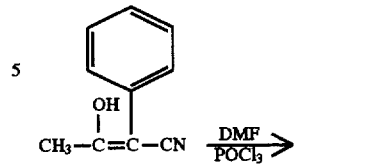

(IIa: R¹' = phenyl; R²' = H, Q' = OH)

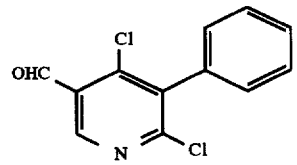

A procedure is followed by analogy with Example 1 with the difference that, instead of 26.8 g (0.4 mol) of allyl cyanide, 79.5 g (0.394 mol) of 78.7% pure 3-hydroxy-2-phenyl-crotononitrile are used. 35.0 g of a crude product are obtained which comprises, according to GC/MS analysis, 78.7% (equivalent to 23.5% of theory) of 2,4-dichloro-3-phenyl-5-pyridinecarboxaldehyde. After recrystallization from cyclohexane, the compound melts at 106° C.

| ¹H—NMR (CDCl₃) | |
|---|---|
| H | δ (ppm) |
| H at C-6 | 8.86(s) |
| CHO | 10.50(s) |

Example 16

(IIa: R¹' = CN; Q' = phenyl; R²' = H)

A mixture of 6.7 g (0.04 mol) of [1-phenyl-ethylidene] malononitrile and 23.4 g (0.32 mol) of DMF was added dropwise with stirring to 49 g (0.32 mol) of phosphorus oxychloride in the absence of moisture at about 95° C. in the course of 15 minutes. The mixture is further stirred for 24 hours at 95° to 100° C. After cooling to about 20° C., the mixture is worked up by analog with Example 1. 5.45 g of a crude product are obtained which, according to GC/MS analysis, contains 50.8% of 2-chloro-3-cyano-4-phenyl-5-pyridinecarboxaldehyde (equivalent to 28.5% of theory). After sublimation at 150° C./0.1 mbar, a colourless sublimate is obtained which, after recrystallization tom cyclohexane, melts at 152° to 153° C. and represents 97.1% pure aldehyde mentioned above.

| ¹H—NMR (CDCl₃) | |
|---|---|
| H | δ (ppm) |
| H at C-6 | 9.09(s) |
| CHO | 9.84(s) |

Example 17

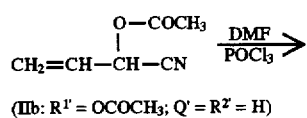

(IIb: R¹ = OCOCH₃; Q' = R² = H)

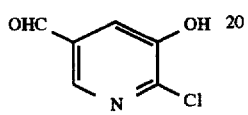

A procedure is followed by analogy with Example 1 with the difference that, instead of 26.8 g (0.4 mol) of allyl cyanide, 62.5 g (0.5 mol) of 2-acetoxy-but-3-enenitrile are used. After cooling to about 20° C., the mixture is first stirred with 500 ml of ethyl acetate and then 500 ml of water are added with cooling in such a manner that the internal temperature does not exceed approximately 25° C. Solid sodium acetate is then added in portions with stirring until a pH of about 5 is attained. The organic phase is separated off and the aqueous phase is further extracted three times, each time with 250 ml of ethyl acetate.

The combined ethyl acetate phases are washed twice each time with 500 ml of water, dried over sodium sulphate and concentrated in a rotary evaporator at 14 mbar up to a bath temperature of 80° C.

Crude 2-chloro-3-hydroxy-5-pyridinecarboxaldehyde remains behind. The compound can be recrystallized, e.g. from toluene, and can be sublimated to pure white at approximately 120° C./0.1 mbar. It darkens from 185° C. and is still not molten at 260° C.

| ¹H—NMR (d₆-DMSO): | |
|---|---|
| H | δ (ppm) |
| H at C-4 | 7.67(d) |
| H at C-6 | 8.42(d) |
| CHO | 10.05(s) |
| OH | 11.3(s) |

Example 18

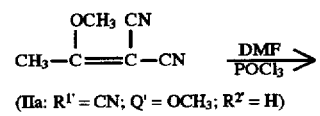

(IIa: R¹ = CN; Q' = OCH₃; R² = H)

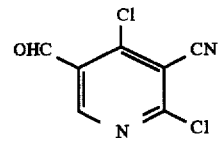

A procedure is followed by analogy with Example 1 with the difference that, instead of 26.8 g (0.4 mol) of allyl cyanide, 61 g (0.5 mol) of (1-methoxyethylidene) malononitrile are used. 59.7 g of a reaction mixture are obtained in which 79.7% of 2,4-dichloro-3-cyano-5-pyridinecarboxaldehyde were detected by GC/MS analysis.

After recrystallization from cyclohexane, pure aldehyde of melting point 128.5°–129° C. was obtained.

| ¹H—NMR (CDCl₃) | |
|---|---|
| H | δ (ppm) |
| H at C-6 | 9.00(s) |
| CHO | 10.45(s) |

Example 19

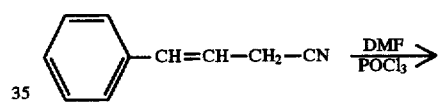

(IIb: R¹ = Q' = H; R² = phenyl)

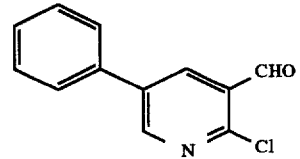

A mixture of 40 g (0.28 mol) of 4-phenyl-but-3-enenitrile and 82 g (1.12 mol) of DMF was added dropwise with stirring to 172 g (1.12 mol) of phosphorus oxychloride in the absence of moisture at about 95° C. in the course of one hour. The mixture is further stirred for 24 hours at 95° to 100° C. After cooling to about 20° C., the mixture is worked up in accordance with Example 1. 47.1 g of 2-chloro-5-phenyl-3-pyridinecarboxaldehyde having a GC purity of 94.7% (equivalent to 73.2% of theory). After recrystallization from petroleum ether, the compound melts at 87° to 87.5° C.

| ¹H—NMR (CDCl₃) | |
|---|---|
| H | δ (ppm) |
| H at C-4 | 8.42(d) |
| H at C-6 | 8.85(d) |
| CHO | 10.51(s) |

Example 20

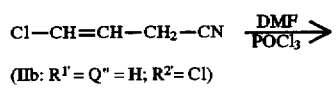

(IIb: R¹' = Q" = H; R²' = Cl)

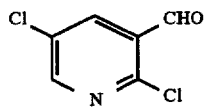

A procedure is followed by analogy with Example 1 with the difference that, instead of 26.8 g (0.4 mol) allyl cyanide, 50.8 g (0.5 mol) of 4-chloro-but-3-enenitrile are used. 70.1 g (79% of theory) of 2,5-dichloro-3-pyridinecarboxaldehyde are obtained having a GC purity of 99.2%. The compound can be sublimated at 100° C./0.1 mbar. Melting point after recrystallization from cyclohexane 93° to 94° C.

| ¹H—NMR (CDCl₃) | |
|---|---|
| H | δ (ppm) |
| H at C-4 | 8.20(d) |
| H at C-6 | 8.60(d) |
| CHO | 10.40(s) |

Example 21

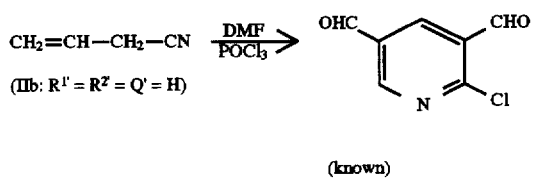

(IIb: R¹' = R² = Q' = H)

(known)

A procedure is followed by analogy with Example 1. To the aqueous phase remaining after shaking with dichloromethane is added in portions solid sodium hydrogencarbonate with stirring and cooling (maximum 25° C.) until a pH of 5 to 6 is attained. The mixture is then further extracted three times each time with 250 ml of dichloromethane and worked up in accordance with Example 1. In this manner a further 7.6 g of 72.6% pure, according to GC, 2-chloro-3, 5-pyridinedicarboxaldehyde are obtained. This increases the overall yield to 58.5% of theory.

Example 22

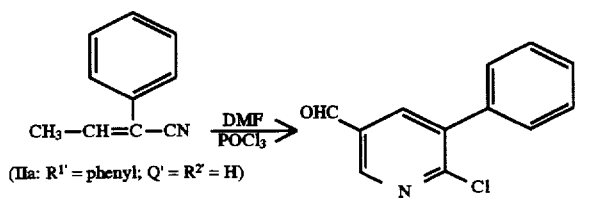

(IIa: R¹' = phenyl; Q' = R² = H)

A procedure is followed by analogy with Example 1 with the difference that, instead of 26.8 g (0.4 mol) of allyl cyanide, 71.5 g (0.375 moo of 75% pure 2-phenyl-but-2-enenitrile are used. 51.4 g of a crude product are obtained which, according to GC-MS analysis, in addition to 37.7% of starting material, contains 43.7% of 2-chloro-3-phenyl-5-pyridinecarboxaldehyde. This is equivalent to a yield of 43.1% of theory, based on reacted starting material. Fractional distillation gives the pyridine at 155° to 160° C./0.05 mbar in 85% GC purity, which solidifies in the refrigerator. After recrystallization from petroleum ether, the compound melts at 69° C.

| ¹H-NMR (CDCl₃) | |
|---|---|
| H | δ (ppm) |
| H at C-4 | 8.14 (d) |
| H at C-6 | 8.86 (d) |
| CHO | 10.15 (s) |

Example 23

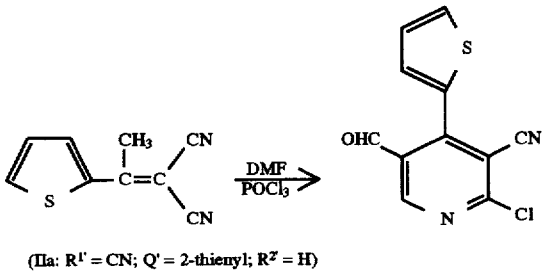

(IIa: R¹' = CN; Q' = 2-thienyl; R² = H)

A procedure is followed by analog with Example 1 with the difference that, instead of 26.8 (0.4 mol) of allyl cyanide, 43.5 g (0.25 mol) of [1-(2-thienyl)ethylidene] propanedinitrile are used. 40.4 g of a crude product are obtained which, according to GC-MS analysis, comprises 78.3% (equivalent to 50.1% of theory) of 2-chloro-3-cyano-4-(2-thienyl)-5-pyridinecarboxaldehyde. After recrystallization from cyclohexane, the compound melts at 137.5° to 138° C.

| ¹H-NMR (CDCl₃) | |
|---|---|
| H | δ (ppm) |
| H at C-6 | 9.03 (s) |
| CHO | 10.04 (s) |

We claim:
1. A process for the preparation of a compound of the formula

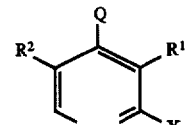

(I)

in which

X denotes chlorine or bromine,

Q denotes hydrogen, halogen, $C_1$–$C_8$-alkyl, cyano-$C_1$–$C_8$-alkyl, $C_1$–$C_4$-alkoxy-$C_1$–$C_8$-alkyl, $C_3$–$C_{10}$-cycloalkyl, $C_6$–$C_{12}$-aralkyl, $C_6$–$C_{12}$-aryl, hetaryl having 5 to 7 ring members and 1 to 3 hetero atoms selected from the group consisting of N, O, or S, $R^1$, $R^2$ denote formyl, cyano, hydroxyl, halogen, $C_1$–$C_8$-alkyl, halogeno-$C_1$–$C_8$-alkyl, cyano-$C_1$–$C_8$-alkyl, $C_1$–$C_4$-alkoxy-$C_1$–$C_8$alkyl, $C_3$–$C_{10}$-cycloalkyl,

$C_6$–$C_{12}$ aralkyl, $C_6$–$C_{12}$-aryl, $C_6$–$C_{12}$-aryloxy, hetaryl having 5 to 7 ring members and 1 to 3 hetero atoms selected from the group consisting of N, O, or S, hetaryloxy having 5 to 7 ring members and 1 to 3 hetero atoms selected from the group consisting of N, O, or S in the hetaryl moiety, with the restriction that at least one of the two substituents $R^1$ and $R^2$ represents formyl, R denotes halogen, $C_1$–$C_4$-alkoxy, phenoxy, —NR'R" and R', R" denote, independently of each other, $C_1$–$C_4$-alkyl or both substituents together denote $C_4$–$C_6$-alkylene which can be interrupted by an oxygen atom, which comprises reacting a compound of the formula

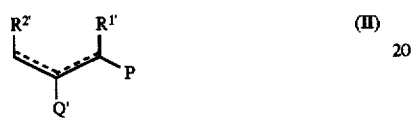

in which the dashed line indicates the two possible positions of a C=C bond,

Q' can assume the meanings defined for Q or denotes hydroxyl or $C_1$–$C_4$-alkoxy, P denotes —CN, —CONH$_2$ or —CH=NOH and R$^{1'}$, R$^{2'}$ denote, independently of each other, hydrogen, cyano, halogen, —CONH$_2$, $C_1$–$C_8$-alkyl, halogeno-$C_1$–$C_8$-alkyl, cyano-$C_1$–$C_8$-alkyl, $C_1$–$C_4$-alkoxy-$C_1$–$C_8$-alkyl, hydroxy-$C_1$–$C_8$-alkyl, $C_1$–$C_8$-alkoxy, $C_3$–$C_{10}$-cycloakyl,

carboxyl, $C_1$–$C_8$-acyloxy, $C_6$–$C_{12}$-aralkyl, $C_6$–$C_{12}$-aryl, $C_6$–$C_{12}$-aryloxy, hetaryl having 5 to 7 ring members and 1 to 3 hetero atoms selected from the group consisting of N, O, or S, hetaryloxy having 5 to 7 ring members and 1 to 3 hetero atoms selected from the group consisting of N, O, or S in the hetaryl moiety with the restriction that at least one of the two substituents R$^{1'}$ and R$^{2'}$ represents hydrogen and R has the meaning specified in formula (I)

with a Vilsmeier reagent wherein when R$^{1'}$ or R$^{2'}$ is hydrogen and P is CN at least 2 mols of the Vilsmeier reagent are used per mol of compound (II) and when R$^{1'}$ or R$^{2'}$ are hydrogen and P is CN, and at least 3 mols of Vilsmeier reagent per mol of compound (II) are employed.

2. The process according to claim 1, wherein Q is hydrogen, halogen, $C_6$–$C_{12}$-aryl or hetaryl having 5 to 7 ring members and 1 to 3 heteroatoms selected from the group consisting of N, O or S.

3. The process according to claim 1 wherein the Vilsmeier reagent is produced from the reaction of a N-formylamide with an acid halide and the N-formylamide is selected from the group consisting of dimethylformamide, N-methylformanilide, N-formylpiperidine, N-formylmorpholine and the acid halide is selected from the group consisting of phosphorus oxychloride, phosphorus oxybromide, phosgene, thionyl chloride, oxalyl chloride.

4. The process according to claim 1, wherein the reaction temperature is 0° to 180° C.

5. A compound of the formula

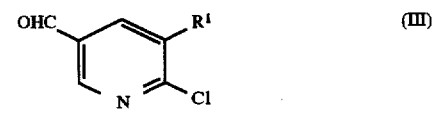

in which $R^1$ represents hydroxy, methyl, phenyl, and chlorocarbonyl.

6. A compound of the formula

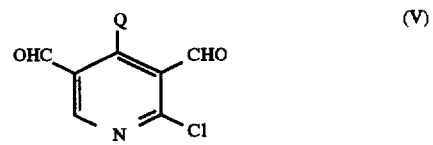

in which

Q represents chlorine or phenyl.

7. A compound of the formula

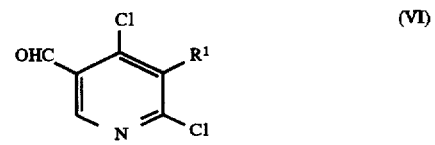

in which $R^1$ represents cyano or phenyl.

* * * * *

UNITED STATES PATENT AND TRADEMARK OFFICE
CERTIFICATE OF CORRECTION

PATENT NO. : 5,708,180
DATED : January 13, 1998
INVENTOR(S) : Beck, et al.

It is certified that error appears in the above-identified patent and that said Letters Patent is hereby corrected as shown below:

Col. 21, line 26    Delete " C=C " and substitute
                    -- C-C --

Signed and Sealed this

Fifth Day of October, 1999

Attest:

Attesting Officer

Q. TODD DICKINSON

Acting Commissioner of Patents and Trademarks